(12) United States Patent
Antel et al.

(10) Patent No.: US 6,930,207 B2
(45) Date of Patent: Aug. 16, 2005

(54) TRIFLUOROACETYLALKYL-SUBSTITUTED PHENYL, PHENOL AND BENZOYL COMPOUNDS AND RELATED METHODS OF TREATMENT

(75) Inventors: Jochen Antel, Bad Muender (DE); Harald Waldeck, Isernhagen (DE); Andreas Potthoff, Hannover (DE); Sabine Irmer, Hannover (DE); Peter-Colin Gregory, Hannover (DE)

(73) Assignee: Solvay Pharmaceutical GmbH, Hannover (DE)

( * ) Notice: Subject to any disclaimer, the term of this patent is extended or adjusted under 35 U.S.C. 154(b) by 0 days.

(21) Appl. No.: 10/758,240

(22) Filed: Jan. 16, 2004

(65) Prior Publication Data

US 2004/0214901 A1 Oct. 28, 2004

Related U.S. Application Data

(63) Continuation of application No. PCT/EP02/07782, filed on Jul. 12, 2002.

(30) Foreign Application Priority Data

Jul. 18, 2001 (DE) .................................. 101 35 027

(51) Int. Cl.[7] .................. C07C 45/00; A61K 31/12
(52) U.S. Cl. ............. 568/314; 568/316; 568/335; 568/336; 514/688; 514/689
(58) Field of Search .................. 568/314, 316, 568/335, 336; 514/688, 689

(56) References Cited

U.S. PATENT DOCUMENTS

| | | | | |
|---|---|---|---|---|
| 3,046,300 A | * | 7/1962 | Sletzinger et al. | 260/471 |
| 4,297,515 A | * | 10/1981 | Eidenschink et al. | 568/329 |
| 4,408,077 A | * | 10/1983 | Sestanj et al. | 568/441 |
| 4,917,826 A | * | 4/1990 | Johnson et al. | 552/522 |

FOREIGN PATENT DOCUMENTS

| | | | |
|---|---|---|---|
| EP | 0289390 | * | 11/1988 |
| EP | 0354548 | * | 2/1990 |
| EP | 0611232 | * | 8/1994 |
| EP | 1167355 | * | 1/2002 |
| FR | 2098305 | * | 3/1972 |
| WO | 89/04819 | * | 6/1989 |
| WO | 98/23605 | * | 6/1998 |
| WO | 99/15129 | * | 4/1999 |
| WO | 00/40569 | * | 7/2000 |
| WO | 02/46129 | * | 6/2002 |

OTHER PUBLICATIONS

Bonnet–Delpon et al. Alpha–Trifluoromethyl–Destabilized Cations: A Route to 1–(Trifluoromethyl)tetralins by Trifluoroacetolysis of 5–Aryl–1,1,1–trifluoropentan–2–ols and Derivatives.☐☐Journal of Organic Chemistry (1988), vol. 53, p 754–759.*

Allen, Karen et al. "Inhibition of Pig Liver Esterase by Trifluoromethyl Ketones: Modulators of the Catalytic Reactors Alter Inhibition Kinetics" *Biochemistry* 1989, 28, pp. 135–140.*

Han, Chang et al. "85–KDA cytosolic phospholipase A2 plays a critical role in PPAR–mediated gene transcription in human hepatoma cells" *Hepatology*, Bd. 34, (4), pt. 2, Oct. 2001.*

Kawase, Masami et al. "Trifluoromethyl ketone–based inhibitors of apoptosis in cerebellar granul neurons" *Biol. Pharm. Bull.* 24(11) 1335–1337 (2001).*

Ghomashchi, F. et al. "Trifluoromethyl ketones and methyl fluorophosphonates as inhibitors of group IV and VI phospholipases $A_2$: structure–function studies with vesicle, micelle, and membrane assays" *Biochimica et Biophysics Acta* 1420 (1999) pp. 45–56.*

Yang, Dan et al. "Regioselective Intramolecular Oxidation of Phenols and Anisoles by Dioxiranes Generated in Situ" *J. Org. Chem.* 2000, 65(13), pp. 4179–4184.*

Begue, Jean Pierre et al. "The Witting Reaction of perfluoro acid derivatives: access to fluorinated enol ethers, enamines, and ketones" *J. Org. Chem.* 1992, 57(14) pp. 3807–3814.

Hammock, Bruce et al. "Trifluoromethylketones as Possible Transition State Analog Inhibitors of Juvenile Hormone Esterase" *Pesticide Biochemistry and Physiology* 1982, 17(1) pp. 76–88.

Pinder, Roger et al. "2–Amino–3–phenyl–1,1,1–trifluoropropanes. Fluorine Analogs of Amphetamines" *Journal of Medicinal Chemistry* 1969, 12(2), pp. 322–324.

Bied, C. et al. "Synthesis and Reactivity of Benzylic and Allylic Samarium Compounds" *Tetrahedron* 1992, 48(19) pp. 3877–3890.

Cheng, C.H. et al. "Polymers Containing Fluorinated Ketone Groups II. NMR Studies of the Reaction of Methylbenzyl Trifluoromethyl Ketones with Alcohols in Carbon Tetrachloride" *Journal of Polymer Sciece: Polymer Chemistry Ed.* 1980, 18(6) pp. 1877–1882.

Biovin, et al. "An Expedient Access to Trifluoromethyl Ketones from Carboxylic Acids" *Tetrahedron Letters* 1992 33(10) pp. 1285–1288.

Wiedemann, J. et al. "Direct Preparation of Trifluoromethyl Ketones from Carboxylic Esters: Trifluoromethylation with (Trifluoromethyl)trimethylsilane" *Angew. Chem. Int. Ed.* 1998, 37(6) pp. 820–821.

(Continued)

*Primary Examiner*—Johann Richter
*Assistant Examiner*—Sikarl A. Witherspoon
(74) *Attorney, Agent, or Firm*—Crowell & Moring LLP

(57) ABSTRACT

Novel and known trifluoroacetyl-substituted phenyl, phenol and benzoyl compounds for the treatment and/or inhibition of obesity and of concomitant and/or secondary diseases involved therewith, in particular metabolic syndrome and cardiovascular diseases. Novel trifluoroacetyl-substituted phenyl, phenol and benzoyl compounds, pharmaceutical preparations containing them and processes for the preparation of these compounds. Also compounds acting as inhibitors of lipase, in particular pancreatic lipase.

31 Claims, No Drawings

OTHER PUBLICATIONS

Kim, S. et al. "Radical–mediated synthesis of trifluoromethyl amines and trifluoromethyl ketones from alkyl iodides" *Tetrahedron Letters* 43 (2002) pp. 7189–7191.

Kawase, M. et al. "alpha–Trifluoromethylated Acyloins Induce Apoptosis in Human Oral Tumor Cell Lines" *Bioorganic & Medicinal Chemistry Letters* 9 (1999) pp. 3113–3118.

Reid, J.C. et al. "Some New β–Diketones Containing the Trifluoromethyl Group" *J. Amer. Chem. Soc.* (1950) 72(7) pp. 2948–2952.

Dale L. Boger et al., "Trifluoromethyl Ketone Inhibitors of Fatty Acid Amide Hydrolase: A Probe of Structural and Conformational Features Contributing to Inhibition", Bioorganic & Medicinal Chemistry Letters 9, 1999, pp. 265–270, XP–004152614.

Burtsev et al., " Factors for the Risk of Acute and Chronic Course of Cerebral Ischemias", Biosciences Information Services, 1990, BIOSIS, Online, Philadelphia, PA, XP–002244872.

\* cited by examiner

TRIFLUOROACETYLALKYL-SUBSTITUTED PHENYL, PHENOL AND BENZOYL COMPOUNDS AND RELATED METHODS OF TREATMENT

CROSS-REFERENCE TO RELATED APPLICATIONS

This application is a continuation of International Patent Application No. PCT/EP02/07782, filed Jul. 12, 2002, designating the United States of America, and published in German as WO 03/007923 A2, the entire disclosure of which is incorporated herein by reference. Priority is claimed based on Federal Republic of Germany Patent Application No. DE 101 35 027.9, filed Jul. 18, 2001.

FIELD OF THE INVENTION

The present invention relates to the use of novel and known trifluoroacetyl-substituted phenyl, phenol and benzoyl compounds for the treatment and/or inhibition of obesity and of concomitant and/or secondary diseases involved therewith, in particular metabolic syndrome and cardiovascular diseases. Furthermore, the invention relates to novel trifluoroacetyl-substituted phenyl, phenol and benzoyl compounds, to pharmaceutical preparations containing them and also processes for the preparation of these compounds. The compounds used according to the invention act as inhibitors of lipase, in particular of pancreatic lipase.

BACKGROUND OF THE INVENTION

Hexadecanoic acid and hexadecadienoic acid derivatives which inhibit pancreatic lipase and therefore can be used in combating or preventing obesity and hyperlipaemias are already known from EP 0 129 748 A1.

Lipase-inhibiting polymers which are suitable for the treatment of obesity are already known from WO 99/34786.

WO 00/40247 and WO 00/40569 describe 2-substituted 4H-3,1-benzoxazin-4-one derivatives which act as lipase inhibitors and which can be used for the treatment of obesity.

Furthermore, WO 99/15129 describes selective cPLA$_2$ inhibitors which also jointly comprise, inter alia, certain trifluoroacetylalkyl-substituted aryl derivatives.

SUMMARY OF THE INVENTION

One object of the present invention is to provide novel lipase-inhibitory pharmaceutical formulations for the treatment and/or inhibition of obesity and its concomitant and/or secondary diseases which are very effective and can be obtained in simple manner.

It has now been found that a group of trifluoroacetylalkyl-substituted phenyl, phenol and benzoyl compounds can act as inhibitors of lipase, in particular of pancreatic lipase. The compounds used according to the invention are thus capable of reducing the lipid digestion induced by pancreatic lipase in mammals, particularly humans, with the result that the body has available overall less usable edible fats. The compounds used according to the invention therefore appear suitable for the treatment and/or inhibition of obesity and illnesses associated therewith. According to the invention, there are used as lipase-inhibitory active substances trifluoroacetylalkyl-substituted phenyl, phenol and/or benzoyl compounds corresponding to formula I, wherein

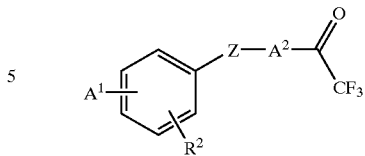

$A^1$ is a group of the formula $R^1$—W—$A^3$—Y—$(CH_2)_n$—, wherein
  $R^1$ is hydrogen,
    lower alkyl,
    $C_{3-7}$-cycloalkyl,
    phenyl-$C_{0-4}$-alkyl, which is optionally substituted in the phenyl ring by lower alkylenedioxy or one to two times by lower alkyl, lower alkoxy, halogen or perfluoro-lower alkyl, or
    naphthyl,
  W is a bond or oxygen,
  $A^3$ is a bond or $C_{1-20}$-alkylene, which is optionally substituted one to two times by phenyl, naphthyl, lower alkyl or $C_{5-7}$-cycloalkyl,
  Y is a bond or oxygen and
  n is a whole number from 0 to 3, and
$R^2$ is hydrogen, lower alkyl, lower alkoxy or halogen, or
$A^1$ and $R^2$, together with the carbon atoms to which they are bonded, form a $C_{5-7}$-cycloalkyl group, the sp$^3$-hybridized carbon atoms of which are optionally replaced one to two times by oxygen,
Z is a bond, oxygen or carbonyl group and
$A^2$ is $C_{1-20}$-alkylene which is optionally substituted once by $C_{1-12}$-alkyl, $C_{1-12}$-alkyl-phenyl or $C_{1-12}$-alkyl-oxyphenyl, for the preparation of pharmaceutical preparations for the treatment and/or inhibition of obesity and its concomitant and/or secondary diseases.

Where in compounds of Formula I or in other compounds described within the scope of the present invention substituents are or contain lower alkyl, these may be straight-chain or branched and possess 1 to 4 carbon atoms. Where substituents are or contain halogen, in particular fluorine, chlorine or bromine are used.

Where in the group $A^1$ the substituent $R^1$ stands for phenyl-$C_{0-4}$-alkyl optionally substituted in the phenyl ring, non-substituted phenyl rings are preferred. Where $R^1$ contains perfluoro-lower alkyl, trifluoromethyl is preferred. Particularly preferred meanings of $R^1$ are hydrogen, lower alkyl, in particular methyl, $C_{3-7}$-cycloalkyl, in particular cyclohexyl, phenyl and naphthyl.

$A^3$ preferably stands for a bond or for unbranched $C_{1-20}$-, in particular $C_{1-7}$-, alkylene.

n preferably stands for a whole number from 0 to 1.

The substituent $R^2$ preferably stands for hydrogen or for halogen, in particular bromine. Where R2 stands for lower alkoxy, methoxy is preferred.

Z preferably means oxygen or carbonyl, in particular carbonyl.

$A^2$ preferably means n-propylene, which is in particular not substituted. Where an alkylene chain $A^2$ is substituted by $C_{1-12}$-alkyl, $C_{1-12}$-alkyl-phenyl or $C_{1-12}$-alkyl-oxyphenyl, in particular n-$C_{1-12}$-alkyl groups of the substituents are used. Where Z stands for carbonyl and $A^2$ is $C_{1-20}$-alkylene substituted once by $C_{1-12}$-alkyl, $C_{1-12}$-alkyl-phenyl or $C_{1-12}$-alkyl-oxyphenyl, preferably the carbon atom of group $A^2$ bound to the carbonyl group Z is substituted.

Compounds of Formula I, wherein substituents, in particular the group $A^1$, are located in the para position relative to the radical "—Z—$A^2$—C(O)—$CF_3$", are preferred.

In one embodiment of the invention, compounds corresponding to formula If are used,

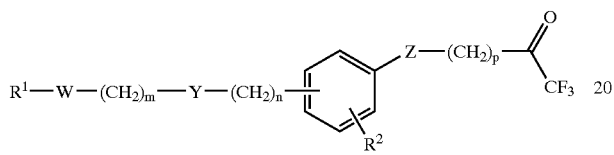

If wherein $R^1$, $R^2$, W, Y and Z have the above meanings, m is a whole number from 0 to 10, n is a whole number from 0 to 3, and p is a whole number from 1 to 20.

Compounds corresponding to formula Ia,

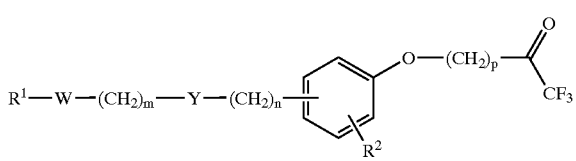

Ia wherein $R^1$, $R^2$, W, Y, m, n and p have the above meanings, are novel compounds and represent a first embodiment of the invention. Preferred compounds of Formula Ia are 5-[4-(benzyloxymethyl)-phenoxy ]-1,1,1-trifluoropentan-2-one; 5-[4-(benzyloxy)phenoxy]-1,1,1-trifluoropentan-2-one; 1,1,1-trifluoro-12-phenoxy-dodecan-2-one and 1,1,1-trifluoro-5-[4-(3-phenylpropoxy)phenoxy]pentan-2-one.

Compounds corresponding to formula Ib,

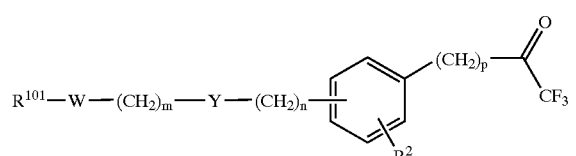

Ib wherein $R^2$, W, Y, m, n and p have the above meanings and $R^{101}$ has the meaning given for $R^1$ with the exception of hydrogen, are novel compounds and represent a second embodiment of the invention. Preferred compounds of Formula Ib are 6-(4-methoxyphenyl)-1,1,1-trifluorohexan-2-one and 5-(4-methoxyphenyl)-1,1,1-trifluoropentan-2-one.

Compounds corresponding to formula Ic,

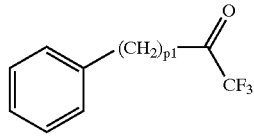

Ic wherein $p^1$ is a whole number from 6 to 20, are novel compounds and represent a third embodiment of the invention. Preferred compounds of Formula Ic are 1,1,1-trifluoro-9-phenyl-nonan-2-one, 1,1,1-trifluoro-11-phenyl-undecan-2-one and 1,1,1-trifluoro-8-phenyl-octan-2-one.

One particularly preferred embodiment of the invention is represented by the compounds corresponding to formula Ig,

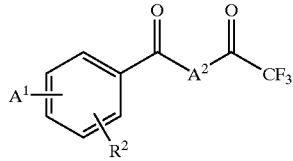

Ig wherein $A^1$, $A^2$ and $R^2$ have the above meanings, and also the solvates and hydrates of compounds of Formula Ig. Compounds of Formula Ig are novel compounds. The compounds of Formula Ig wherein $A^2$ stands for optionally substituted n-propylene have proved particularly beneficial. Preferred compounds which come under Formula Ig are for example 6,6,6-trifluoro-1-(4-methoxyphenyl)hexan-1,5-dione; 6,6,6-trifluoro-1-(4-(4-phenoxybutoxy)phenyl)hexane-1,5-dione; 6,6,6-trifluoro-1-(4-(3-phenylpropoxy)phenyl)hexane-1,5-dione; 1-(4-bromophenyl)-6,6,6-trifluorohexane-1,5-dione; 6,6,6-trifluoro-1-(4-(1-naphthyl)phenyl)hexane-1,5-dione; 6,6,6-trifluoro-1-(5,6,7,8-tetrahydronaphthalen-2-yl)hexane-1,5-dione; 6,6,6-trifluoro-1-(4-(4-methoxy-1-naphthyl)phenyl)hexane-1,5-dione; 6,6,6-trifluoro-1-(4-(2-naphthyl)phenyl)hexane-1,5-dione; 6,6,6-trifluoro-1-(4-(hexadecyloxy)phenyl)hexane-1,5-dione and 6,6,6-trifluoro-1-(4-(tetradecyloxy)phenyl) hexane-1,5-dione. One subgroup of the compounds of Formula Ig is represented by the compounds corresponding to formula Id,

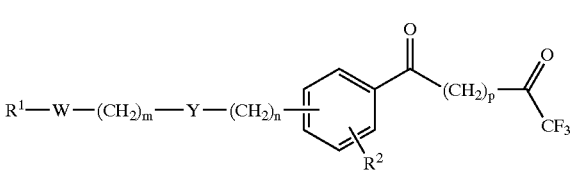

Id wherein $R^1$, $R^2$, W, Y, m, n and p have the above meanings.

Compounds corresponding to formula Ie,

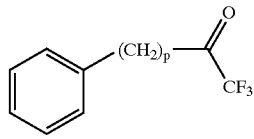

Ie wherein p has the above meaning, are partially already known per se, for example from J. Boivin et al., Tetrahedron Letters 33 (1992) 1285–1288 (cited below as "J. Boivin et al."), from R. P. Singh et al., Journal of Organic Chemistry 64 (1999) 2873–2876 (cited below as "R. P. Singh et al.") or from EP 0 434 297 A2, and may for example be prepared according to the processes described therein or to analogous processes. The use of the compounds of Formula Ie in pharmaceutical formulations has not been described hitherto. The subject of the invention is therefore also compounds of Formula Ie for use in pharmaceutical formulations.

The compounds of Formula I may be prepared by
a) reacting a compound corresponding to formula XIa,

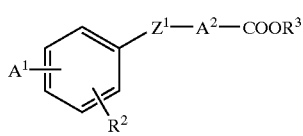
XIa wherein $A^1$, $A^2$ and $R^2$ have the above meanings, $R^3$ stands for lower alkyl and $Z^1$ is a bond or oxygen, with (trifluoromethyl)trimethylsilane ($=CF_3TMS$), or
b) reacting a compound corresponding to formula XIb

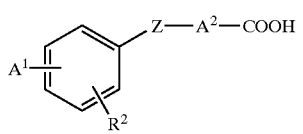
XIb wherein $A^1$, $A^2$, $R^2$ and Z have the above meanings, with an acetic anhydride derivative and reacting optionally En-lactones obtained as intermediate products with (trifluoromethyl)trimethylsilane according to process variant a).

The reaction of esters of Formula XIa with $CF_3TMS$ according to process variant a) can take place in known manner, for example according to the process described in R. P. Singh et al. or analogous processes. To this end, compounds of Formula XIa may be reacted with $CF_3TMS$, preferably in the presence of an alkali metal fluoride salt, in particular cesium fluoride, and with the exclusion of aqueous moisture in an organic solvent which is inert under the reaction conditions. Suitable solvents are polar or non-polar aprotic solvents, for example glycol ethers such as 1,2-dimethoxyethane ("glyme"). The resulting intermediate product can then be cleaved in situ, for example by addition of acid or by addition of fluorides, in particular tetrabutylammonium fluoride (TBAF), to form the desired compound of Formula I. Suitable acids for cleavage are protonic acids, for example hydrochloric acid. The reaction may preferably be carried out at room temperature (RT) and under a protective gas atmosphere.

The reaction of carboxylic acids of Formula XIb with an acetic anhydride derivative according to process variant b) can take place in known manner, for example according to the process described in J. Boivin et al. or analogous processes. To this end, compounds of Formula XIb may be reacted with an acetic anhydride derivative such as trifluoroacetic anhydride (TFAA) or acetic anhydride, preferably in the presence of a non-nucleophilic organic base, for example an organic amine or pyridine, in an organic solvent which is inert under the reaction conditions. Suitable solvents are polar aprotic solvents such as haloalkanes, preferably dichloromethane. It is beneficial to carry out the reaction under a protective gas atmosphere and with aqueous moisture excluded. The reaction temperature may be between about –b 20° C. and 120° C., depending on the acetic anhydride derivative used. If TFAA is used, the reaction temperature may be between –20° C. and room temperature, preferably at 0° to 5° C. If acetic anhydride is used, the reaction temperature may be between 80° C. and 120° C., preferably 90° to 110° C. The resulting intermediate product can then be hydrolyzed by addition of water, preferably ice water, to form the desired compound of Formula I. Where the reaction of carboxylic acids of Formula XIb, wherein Z stands for carbonyl, with TFAA does not lead directly to the preparation of compounds of Formula I, intermediate products such as unsaturated lactones of the carboxylic acids of Formula IIb may still be produced. These intermediate products may be converted into the desired compounds of Formula I in known manner, for example in accordance with process variant a) given above. In one embodiment for the preparation of compounds of Formula If, compounds corresponding to formula IIa,

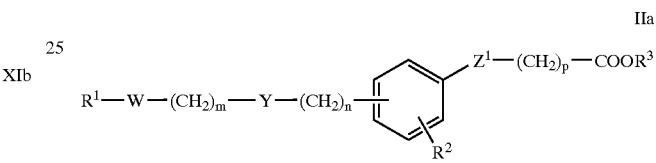
IIa wherein $R^1$, $R^2$, $R^3$, W, Y, $Z^1$, m, n and p have the above meanings, can be used in the manner stated above for process variant a) analogously to the compounds of Formula XIa, or compounds corresponding to formula IIb,

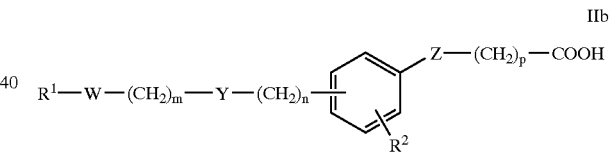
IIb wherein $R^1$, $R^2$, W, Y, Z, m, n and p have the above meanings, can be used in the manner stated above for process variant b) analogously to the compounds of Formula XIb.

The esters of Formula XIa and the acids of Formula XIb are known per se or may be prepared by the person skilled in the art according to known processes from known starting compounds. Thus for example compounds corresponding to formula XIc,

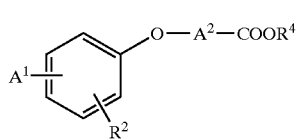
XIc wherein $A^1$, $A^2$, and $R^2$ have the above meanings and $R^4$ is hydrogen or lower alkyl, can be prepared by reacting a compound corresponding to formula XII,

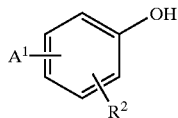

XII wherein $A^1$ and $R^2$ have the above meanings, with a compound corresponding to formula V, $$X-A^2-COOR^3 \qquad V$$

wherein $A^2$ and $R^3$ have the above meanings and X stands for a leaving group, in particular halogen, and subsequently if desired removing a lower alkyl group $R^3$ again in a manner known for ester cleavage. The bromides of Formula V are preferred. The reaction can take place in a manner known for nucleophilic substitutions. For example, the reaction may be carried out in an organic solvent which is inert under the reaction conditions such as a dipolar aprotic solvent, preferably tetrahydrofuran (THF) or dimethyl formamide (DMF), and in the presence of a suitable non-nucleophilic organic base, preferably potassium tert. butylate or sodium hydride. The reaction is usually conducted at temperatures between about −40° and 80° C. In one special embodiment of this variant, a compound corresponding to formula IIe,

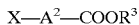

IIe wherein $R^1$, $R^2$, $R^4$, W, Y, m, n and p have the above meanings, can be prepared by reacting a compound corresponding to formula IV

IV wherein $R^1$, $R^2$, W, Y, m and n have the above meanings, with a compound corresponding to formula Va, $$X-(CH_2)_p-COOR^3 \qquad Va$$

wherein $R^3$, p and X have the above meanings, and subsequently if desired cleaving a lower alkyl group $R^3$ again in a manner known for ester cleavage.

The compounds of Formulae IV, V, Va and XII are known per se or can be prepared from known compounds in known manner.

Compounds of Formula XId,

XId wherein $A^1$, $A^2$, $R^2$, and $R^4$ have the above meanings, can for example be prepared by reacting a compound corresponding to formula XIII,

XIII wherein $A^1$ and $R^2$ have the above meanings, with a compound corresponding to formula VII, $$X^3OC-A^2-COOR^{301} \qquad VII$$

wherein $A^2$ has the above meaning, $R^{301}$ has the meaning given above for $R^3$ or together with $X^3$ forms a cyclic anhydride, and $X^3$ has the above meaning or is also halogen, in particular chlorine or bromine, and subsequently if desired removing a lower alkyl group $R^{301}$ again in a manner known for ester cleavage. The reaction can be carried out in known manner, for example under the conditions known for Friedel-Crafts acylations in an organic solvent which is inert under the reaction conditions such as a haloalkane, preferably dichloromethane, and with catalysis by a Lewis acid such as aluminum trichloride. Compounds of Formula VII are known per se or can be prepared from known starting compounds in known manner. Preferred compounds of Formula VII are for example glutaric anhydride or glutaric acid monoethylester chloride. Those cases in which compounds of Formula XIII are particularly suitable as starting compounds for the preparation of compounds of Formula XId by Friedel-Crafts acylation because of their substitution pattern are familiar to the person skilled in the art. Compounds of Formula XIII are known per se or can be prepared from known starting compounds in known manner. Thus for example compounds of Formula XIII, wherein $A^1$ is a group of the formula $R^1-W-A^3-Y-(CH_2)_n-$ and wherein n is not 0 or Y stands for a bond, may be obtained by a Wittig reaction of a benzaldehyde derivative substituted by $R^2$ with a phosphonium salt or phosphonate suitable for introducing an aforementioned group $A^1$ in the presence of a base and subsequent hydrogenation of the intermediate alkene obtained.

Where a $C_{1-12}$-alkyl group, a $C_{1-12}$-alkyl-phenyl group or a $C_{1-2}$-alkyl-oxyphenyl group is to be introduced into a compound of Formula XId, wherein $A^2$ stands for non-substituted $C_{1-20}$-alkyl and $R^4$ stands for lower alkyl, this can be accomplished in known manner by a nucleophilic substitution reaction. In particular, an aforementioned compound of Formula XId may be deprotonated by reacting with a non-nucleophilic base such as sodium hydride in a solvent which is inert under the reaction conditions such as DMF and then alkylated with a reactive reagent suitable for introducing a $C_{1-12}$-alkyl group, a $C_{1-12}$-alkyl-phenyl group or a $C_{1-12}$-alkyl-oxyphenyl group. Suitable reactive reagents for the alkylation are, for example, terminal halogens, in particular terminal bromides of the aforementioned groups. The alkyl substitution takes place in this procedure usually on the aliphatic carbon atom of the compound of Formula XId which is adjacent to the carbonyl group Z.

In a special embodiment of the preparation of compounds of Formula XId, a compound corresponding to formula IIf,

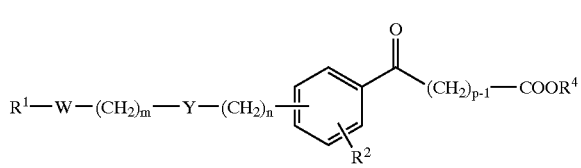

IIf wherein $R^1$, $R^2$, $R^4$, W, Y, m, n and p have the above meanings, can be prepared by reacting a compound corresponding to formula VI,

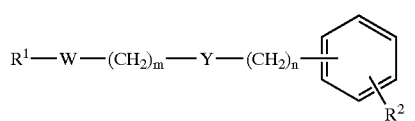

VI wherein $R^1$, $R^2$, W, Y, m and n have the above meanings, with a compound corresponding to formula VIIa,

VIIa wherein $R^{301}$, $X^3$ and p have the above meanings, in the manner described above and subsequently if desired removing a lower alkyl group $R^3$ again in a manner known for ester cleavage.

Compounds of Formula IIf can also be prepared by oxidizing a compound corresponding to formula VIII,

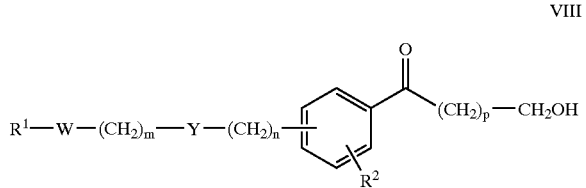

VIII wherein $R^1$, $R^2$, W, Y, m, n and p have the above meanings, at the primary alcohol function and if desired also esterifying the carboxy group produced by oxidation. The oxidation can be carried out in a manner known for converting primary alcohols into carboxylic acids, for example by reacting the compounds of Formula VIII with chromium (VI) oxide.

Compounds of Formula VIII can be prepared for example by reacting a compound corresponding to formula IX,

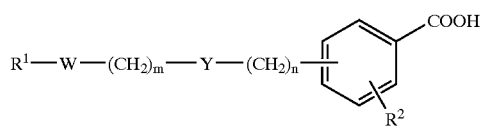

IX wherein $R^1$, $R^2$, W, Y, m and n have the above meanings, with a compound corresponding to formula X,

X wherein p has the above meaning, $X^1$ is halogen and SG stands for a cleavable protective group, and subsequently cleaving a protective group SG again in known manner. The bromides and iodides of Formula X are preferred. The reaction may take place in a manner known for performing Grignard reactions. In particular, in each case one equivalent of a compound of Formula IX is reacted with two equivalents of a compound of Formula X. Suitable protective groups SG are known, for example, from J. A. W. McOmie "Protective Groups in Organic Chemistry", Plenum Press 1973, or from T. W. Green and P. G. Wuts "Protective Groups in Organic Synthesis", Wiley and Sons 1999. The person skilled in the art can select suitable protective groups for each case by routine methods.

The compounds of Formula IX and the compounds of Formula X are known per se or can be prepared in known manner from known compounds.

In one variant, compounds of Formula XId can be prepared by reacting a compound corresponding to formula XIV,

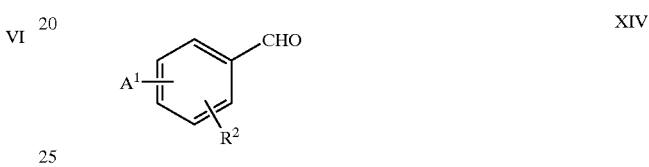

XIV wherein $A^1$ and $R^2$ have the above meanings, with a compound of Formula V and subsequently if desired cleaving a lower alkyl group $R^3$ again in a manner known for ester cleavage. The reaction may be carried out in a known manner in an organic solvent which is inert under the reaction conditions such as a cyclic or open-chain di-lower alkyl ether, preferably THF. In particular, an aldehyde of Formula XIV can first be converted in the presence of catalytic reagents such as TBAF and trimethylsilyl cyanide at a temperature between −100° C. and −60° C. into a silylated cyanohydrin intermediate product which after deprotonation by a non-nucleophilic base, preferably an organic base such as lithium-bis(trimethylsilyl)amide or lithium diisopropylamide (LDA) and at elevated temperature, preferably RT, then can be reacted with a compound of Formula V. Compounds of Formula XIV are known per se or can be prepared from known starting compounds in known manner.

In a further variant, compounds of Formula XId can be prepared by oxidizing a compound corresponding to formula XV,

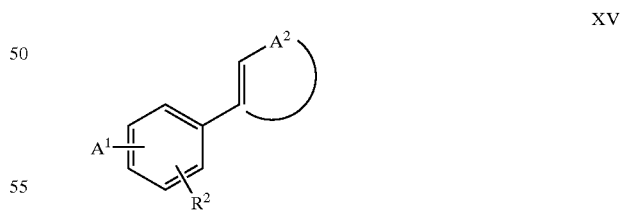

XV wherein $A^1$, $A^2$ and $R^2$ have the above meanings, with a suitable oxidizing agent. The oxidation can be carried out in known manner in an organic solvent which is inert under the reaction conditions such as an aromatic solvent, in particular toluene, at temperatures between −20° C. and room temperature. Suitable oxidizing agents are for example potassium permanganate, preferably in the presence of a phase transfer catalyst such as Aliquat® 336. Likewise, the oxidation can be carried out by ozonolysis with subsequent working-up in the presence of an oxidizing agent.

Compounds of Formula XV can be prepared by reacting a compound corresponding to formula XVII,

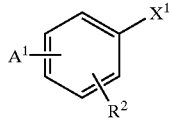

wherein $A^1$, $R^2$ and $X^1$ have the above meanings, with a cyclic ketone corresponding to formula XVIII,

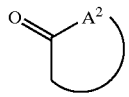

wherein $A^2$ has the above meaning, in known manner under the conditions of a Grignard reaction, and then reacting the resulting intermediate product by acid-catalyzed water cleavage to form a compound of Formula XV.

Compounds corresponding to formula XIe,

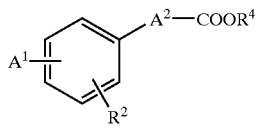

wherein $A^1$, $A^2$, $R^2$ and $R^4$ have the above meanings, can for example be prepared by selectively hydrogenating a carbonyl group Z in a compound of Formula XId in known manner. The hydrogenation can be carried out in an organic solvent which is inert under the reaction conditions such as ethyl acetate (EA) as a heterogeneously catalyzed hydrogenation. Suitable catalysts are e.g. heterogeneous precious-metal catalysts such as palladium on activated carbon. In a special embodiment of this variant for the preparation of compounds of Formula XIa, a compound corresponding to formula IIg,

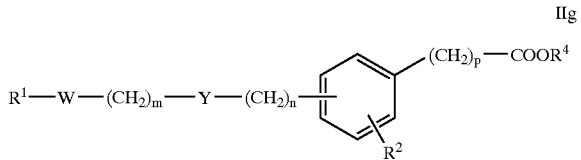

wherein $R^1$, $R^2$, $R^4$, W, Y, m, n and p have the above meanings, can be prepared by selectively hydrogenating a corresponding compound of formula IIf.

For the preparation of compounds of Formula I, wherein $A^1$ stands for a group of formula $R^1$—W—$A^3$—Y—$(CH_2)_n$—, the group $A^1$ may if desired be introduced in various ways into suitable precursor compounds of the compounds of Formula I in each case. Known reactions are suitable for this according to the structure of the group $R^1$—W—$A^3$—Y—$(CH_2)_n$— which is to be introduced.

For the preparation of compounds of Formula I, wherein Y is oxygen, the group of formula $R^1$—W—$A^3$—Y—$(CH_2)_n$— may for example be built up by coupling a group of formula $R^1$—W—$A^3$— in the form of a reactive derivative suitable for coupling, such as a halogen derivative, with a suitable precursor compound of Formula I which is additionally substituted in the phenyl ring bearing the group $R^2$ by HO—$(CH_2)_n$—. The precursor compounds of Formula I which are additionally substituted in the phenyl ring bearing the group $R^2$ by HO—$(CH_2)_n$— may themselves represent compounds of Formula I. The coupling can be carried out in the manner of ether formation, for example by nucleophilic substitution reaction. In an exemplary embodiment of the aforementioned ether formation, a compound corresponding to formula IIc

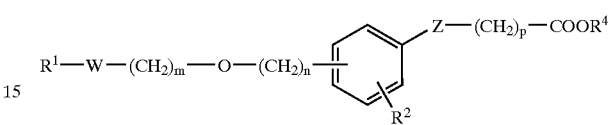

wherein $R^1$, $R^2$, $R^4$, W, Z, m, n and p have the above meanings, can be prepared by reacting a compound corresponding to formula IId

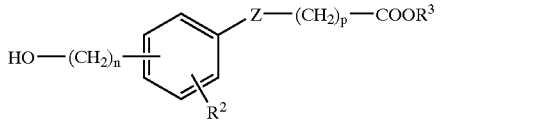

wherein $R^2$, $R^3$, Z, n and p have the above meanings, with a compound corresponding to formula III,

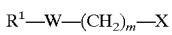

$$R^1\text{—W—}(CH_2)_m\text{—X} \qquad III$$

wherein $R^1$, W, X and m have the above meanings, and subsequently if desired cleaving a lower alkyl group $R^3$ again.

For the preparation of compounds of Formula I, the group of formula $R^1$—W—$A^3$—Y—$(CH_2)_n$— may for example be introduced by coupling the group of formula $R^1$—W—$A^3$—Y—$(CH_2)_n$— in the form of a reactive derivative suitable for coupling, such as a boronic acid derivative, with a suitable precursor compound of Formula I which is substituted in the phenyl ring bearing the group $R^2$ by a suitable leaving group such as halogen or the trifluoromethanesulphonyl group, by a reaction catalyzed by precious metal, preferably Pd(0). Such coupling reactions catalyzed in particular by Pd(0)- are known per se, for example in the form of Heck, Stille or Suzuki couplings. Precursor compounds of Formula I suitable for performing the Pd(0)-catalyzed coupling reactions and reactive derivatives of the group of formula $R^1$—W—$A^3$—Y—$(CH_2)_n$— are known to the person skilled in the art or can be found by routine methods. The precursor compounds of Formula I which are substituted in the phenyl ring bearing the group $R^2$ by halogen may themselves represent compounds of Formula I.

Further compounds of Formulae XIa and XIb may be prepared in known manner corresponding to the preparation processes described above or analogously to these preparation processes.

Furthermore, compounds of Formula I can be prepared analogously to processes described in WO 99/15129 or in EP 0 434 297 A2.

The compounds of Formula I may be isolated from the reaction mixture and purified in known manner.

The present invention covers, in addition to the free compounds of Formula I which contain a trifluoroacetyl group, also compounds of Formula I which are solvated, in particular hydrated, at the trifluoroacetyl group.

Furthermore, the invention also covers precursor compounds of compounds of Formula I which are modified at the keto function of the trifluoroacetyl group by groups which are readily cleavable, releasing the keto function—such as trifluoroacetyl enol ester derivatives, enol phosphate derivatives, cyclic or open-chain substituted or non-substituted O,O-ketals, O,S-ketals, O,N-ketals or S,N-ketals, cyclic glycolates, thioglycolates, glyoxylates or oxalates. These, and other, groups which are readily cleavable—for example under physiological conditions in vivo—releasing the keto function are known to the person skilled in the art, as is their routine introduction and their cleavage in order to obtain compounds of Formula I.

The compounds of Formula I according to the invention are suitable for the inhibition of lipase, in particular for the optionally selective inhibition of pancreatic lipase of larger mammals, particularly humans. Compounds with lipase-inhibiting properties are capable, if supplied to the digestive tract preferably together with fat-containing food, of reducing the proportion of the edible fats actually digested by the body in the total edible fats ingested. In this manner, fat resorption in mammals, particularly humans, can be reduced. The group of compounds according to the invention thus appears suitable for the treatment and/or inhibition of obesity and of concomitant and/or secondary diseases involved therewith. The concomitant diseases of obesity or the secondary diseases thereof which can each be treated with the compounds according to the invention include in particular metabolic syndrome and cardiovascular diseases. The term "metabolic syndrome" usually covers a complex of clinical pictures which mainly comprise hypertension, in particular arterial hypertension, insulin resistance, in particular diabetes mellitus type II, dyslipoproteinaemia, in particular as hypertriglyceridaemia, accompanied by dyslipoproteinaemia occurring lowered HDL-cholesterol, and also hyperuricaemia, which can lead to gout. The term "cardiovascular diseases" in conjunction with obesity is usually understood to mean coronary heart disease, which can lead to heart failure, cerebrovascular diseases, which may for example be accompanied by an increased risk of strokes, and peripheral occlusive arterial disease. Further concomitant and/or secondary diseases of obesity may be gall-bladder diseases such as formation of gallstones, sleep apnea syndrome, orthopedic complications such as osteoarthritis and psychosocial disorders.

The lipase-inhibiting properties of the compounds of Formula I can be demonstrated e.g. by an in vitro activity test. In this test the inhibition of the lipolytic action of porcine pancreatic lipase with respect to the test substrate p-nitrophenyl palmitate under the influence of the test substances of Formula I was determined. Therein, the change in the relative extinction of the investigated solutions caused by the lipolytic release of p-nitrophenol from p-nitrophenyl palmitate was measured. The residual activity of the lipase remaining after the addition of the test substances is given in percent, relative to the original initial lipolytic activity. The example numbers quoted relate to the preparation examples given below.

The reagents given below are prepared:

1. Substrate Solution
   For the preparation of a "solution A", 45 mg p-nitrophenyl palmitate was dissolved in 15 ml isopropanol by sonication with ultrasound. For the preparation of a "solution B" 310 mg Na-deoxycholate dry substance and 150 mg gum arabic were dissolved in 135 ml 0.05 M sodium phosphate buffer (pH=8.0). 5 minutes before the test was performed, 9 ml "solution B" was mixed with 1 ml "solution A" to form a "solution C" and brought to a temperature of 38° C.

2. Pancreatic Lipase Solution
   100 mg FIP-lipase standard LS7 (porcine pancreatic lipase, 36,700 FIP units/g) were dissolved in 50 ml ice-cold 1%-strength aqueous sodium chloride solution and filtered through a 0.2 $\mu$m-syringe filter. After determination of the lipase activity in accordance with FIP, the solution was set to an activity of 40 FIP units/ml with 1%-strength aqueous sodium chloride solution. Dilute pancreatic lipase solutions which had activities of in each case 10, 20 and 30 FIP units/ml were also prepared from the pancreatic lipase solution for a calibration series by diluting with 1%-strength aqueous sodium chloride solution.

3. Inhibitor Solutions
   The lipase-inhibitory compounds of Formula I were dissolved in various concentrations in dimethyl sulfoxide (DMSO), so that between 2.0 and 800 nmol of the inhibitor were present in 100 $\mu$l inhibitor solution. Pure DMSO was used to determine the blank reading.

Performance of the Test

100 $\mu$l of the inhibitor solution of a given concentration prepared as described above was temperature-controlled for 5 minutes in the cell changer of a photometer (Biochrom 4060). Then 1 ml of the above "solution C" was added with stirring. Then the reaction was started by addition of 100 $\mu$l pancreatic lipase solution with stirring. 2 minutes after the start of the reaction, the extinction of each sample was detected for 4 minutes at 405 nm.

In each case, in addition to the sample measurement, a calibration series was also measured to determine the lipase activity. The calibration samples did not contain any inhibitor, but pancreatic lipase solution of differing activities (10, 20, 30 and 40 FIP units/ml, see above). The calibration series served to determine the lipase activity. To determine the calibration series, the lipase units used were plotted against the extinction values (dE/min) determined in each case. Using these calibration lines and the extinction values determined for the respective incubation batches, the lipase activity can be determined for each sample. The residual activity and hence the inhibitory action of the test substances can be calculated according to the lipase activity used. To determine the blank reading, 100 $\mu$l DMSO were mixed with 1 ml "solution C" and the reaction was started by addition of 100 $\mu$l of a lipase solution.

Evaluation of the Test

The measured value of the photometer per batch (dE/min.) is yielded by the difference in the extinction values after the second and sixth minute (dE) divided by the measuring time (dt=4 min.). The blank reading is determined analogously and then subtracted from the measured value. The residual activity can be read off via the calibration line by means of the dE value calculated in this manner.

In the pancreatic lipase activity test set forth above, the test substances given below each in a concentration (c) of 0.727 $\mu$M (unless otherwise stated) caused an inhibition of the lipase activity to the fraction of the original initial activity given below. The compounds of Examples 17, 28, 29, 32, 39, 40, 47, 48, 56, 58 and 59 were measured in a concentration of 0.364 $\mu$M each time. The compounds of Examples 21, 35, 37, 38, 49, 50, 51, 54, 55 and 64 were measured in a concentration of 0.182 $\mu$M each time. The compounds of Examples 46, 61, 62 and 65 were measured in a concentration of 0.091 $\mu$M each time. The example numbers quoted relate to the preparation examples given below.

The compounds of Examples 1–14, 16–23, 25–29, 31–32, 37–41, 44–51, 54–59 and 61–62 caused inhibition of the lipase activity to at most 60% of its original initial activity.

The compounds of Examples 1–4, 6, 9–10, 16–19, 21–23, 26–28, 32, 35, 37–41, 44, 45, 47, 49, 51, 54, 55, 57 and 58 caused inhibition of the lipase activity to at most 35% of its original initial activity.

The compounds of Examples 4, 32, 34, 37, 38, 40, 41, 44, 47, 51, 54, 55, 57–62 and 65 caused inhibition of the lipase activity to at most 20% of its original initial activity.

The compounds of Formula I may be administered in conventional pharmaceutical preparations. The doses to be used may vary individually and will naturally vary according to the type of condition to be treated and the substance used. In general, however, medicinal forms with an active substance content of 10 to 500 mg, in particular 50 to 250 mg, active substance per individual dose are suitable for administration to humans and larger mammals.

The compounds may be contained according to the invention, together with conventional pharmaceutical auxiliaries and/or carriers, in solid or liquid pharmaceutical preparations. Examples of solid preparations are preparations which can be administered orally, such as tablets, coated tablets, capsules, powders or granules. These preparations may contain conventional inorganic and/or organic pharmaceutical carriers, such as talcum, lactose or starch, in addition to conventional pharmaceutical auxiliaries, for example lubricants or tablet disintegrating agents. Liquid preparations such as suspensions or emulsions of the active substances may contain the usual diluents such as water, oils and/or suspension agents such as polyethylene glycols and the like. Other auxiliaries may additionally be added, such as preservatives, taste correctives and the like.

The active substances may be mixed and formulated with the pharmaceutical auxiliaries and/or carriers in known manner. For the production of solid medicament forms, the active substances may for example be mixed with the auxiliaries and/or carriers in conventional manner and may be wet or dry granulated. The granules or powder may be poured directly into capsules or be pressed into tablet cores in conventional manner.

The preparation examples for the preparation of compounds corresponding to formula I given below are intended to explain the invention further, without limiting its scope.

EXAMPLE 1

5-{4-[(benzyloxy)-methyl]-phenoxy}-1,1,1-trifluoropentan-2-one

A) 100 g 4-hydroxybenzyl alcohol was dissolved in 600 ml dried DMF and 213.2 g ground, dried potassium carbonate was added thereto. 126 ml of ethyl 4-bromobutyrate was added to this receiving solution with moisture excluded. Then the resulting reaction mixture was stirred for 18 hours (h) at room temperature and 4 h at 45° C. After cooling to room temperature, it was diluted with methyl tert. butylether (MTBE) and the precipitate was removed by suction. The filtrate was reduced under reduced pressure and the residue was taken up with a 1:1-mixture of EA and MTBE. The resulting solution was then washed with ice water, dilute aqueous sodium hydroxide solution and saturated common salt solution. The organic phase, after drying over sodium sulfate, was evaporated in a vacuum and the resulting residue was crystallized from 300 ml of a solvent mixture of 95% n-hexane and 5% MTBE. The resulting crystals were separated from the mother lye by vacuum filtration and dried in a vacuum at 30° C. A total of 154.7 g ethyl 4-[4-(hydroxymethyl)phenoxy] butyrate was obtained, melting point (m.p.)=34–36° C.

B) 11.9 g of the product obtained above was dissolved in 120 ml dry tetrahydrofuran (THF) under a protective gas atmosphere and cooled to −30° C. For this, a solution of 5.7 g potassium tert. butylate in 50 ml dry THF was added dropwise. After one hour's stirring, a solution of 6.1 ml benzyl bromide in 10 ml dry THF was added at this temperature. It was stirred for 1 hour at −30° C., allowed to reach 0° C. and then diluted with 150 ml MTBE. After washing with potassium hydrogen sulfate solution and water, the organic phase was dried over sodium sulfate and evaporated at reduced pressure. The resulting residue was purified on silica gel with a mobile solvent mixture consisting of 4 parts n-hexane and one part EA. Evaporation and drying of the product fractions in a vacuum yielded 5.8 g ethyl 4-{4-[(benzyloxy)methyl] phenoxy}butyrate, IR (film): 2937, 2859, 1733, 1612, 1513, 1247 cm$^{-1}$.

C) 5.6 g of the product obtained above was dissolved in 25 ml 1,2-dimethoxyethane ("glyme"), which had previously been dried over an activated molecular sieve, under a protective gas atmosphere. To this, first 2.55 ml (trifluoromethyl)trimethylsilane and then 20 mg dried cesium fluoride were rapidly added with stirring. The resulting reaction mixture was stirred for 2 h at RT. Then 5.4 g TBAF was added to this solution and it was stirred for a further 2 h at RT. The reaction mixture was then diluted with 50 ml MTBE and washed with water. The organic phase was dried over sodium sulfate and evaporated under reduced pressure. The remaining residue was flash-chromatographed on 200 g silica gel with a mobile solvent mixture consisting of 4:1 n-hexane and ethyl acetate. After evaporating the product fractions and drying in a vacuum at 60° C., 4.2 g of the title compound was obtained as an oil, IR (film): 3033, 2940, 2861, 1764, 1612, 1587, 1513, 1208 cm$^{-1}$; mass spectrum (MS) m/z: 352, 261, 107, 91.

EXAMPLE 2

1,1,1 -trifluoro-6-(4-methoxyphenyl)-hexan-2-one

A) 16.3 ml anisole was added to a solution of 11.4 g glutaric anhydride in 250 ml dichloromethane. Then 26.7 g anhydrous aluminum trichloride was added in portions with ice cooling. The reddish-colored reaction mixture was stirred for 3 h at 0° C. and then poured on to a mixture of ice and dilute hydrochloric acid. The resulting white precipitate was removed by suction under vacuum, washed with water and dichloromethane and finally dried at reduced pressure at 60° C. 13.6 g 5-(4-methoxyphenyl)-5-oxo-valeric acid, m.p.=139–142° C., was obtained.

B) 4.4 g of the product obtained above was dissolved in a solvent mixture consisting of 200 ml EA and 50 ml glacial acetic acid. After the addition of 0.16 g palladium catalyst (10% on carbon), the mixture was hydrogenated at 2.5 bar hydrogen pressure and 50° C. for eight hours. After filtering the catalyst and subsequently washing with EA, evaporation was carried out at reduced pressure and the crude product was filtered over a silica gel column for further purification (mobile solvent: dichloromethane/methanol 9:1). After drying in a vacuum, 4.2 g 5-(4-methoxyphenyl)-valeric acid, m.p.=107–111° C., was obtained.

C) A solution of 2.0 g of the product obtained above in 20 ml dry dichloromethane was added dropwise to a solution of 8.2 ml trifluoroacetic anhydride in 10 ml dry dichloromethane under a protective gas atmosphere and with ice cooling, the temperature not exceeding 5° C. After cooling to 0° C., 7.15 ml pyridine were added dropwise. The reaction mixture was then stirred for one hour at 0° C. and for two hours at RT. Then 80 ml ice water was slowly added and stirred for 30 minutes with cooling. Water was added thereto and the aqueous phase was extracted with dichloromethane. The organic phase was then washed with saturated sodium chloride solution and dried over sodium sulfate. The organic phase was then evaporated under reduced pressure. The resulting residue was flash-chromatographed on silica gel (mobile solvent: initially n-hexane, which was continuously replaced by EA). Evaporation of the product fractions yielded 1.1 g of the title compound as oil, IR (film): 2937, 2860, 1764, 1613, 1584, 1513, 1209, 827, 709 cm$^{-1}$; MS m/z: 260, 191, 147, 121, 91.

EXAMPLE 3

5-[4-(benzyloxy)phenoxy]-1,1,1-trifluoropentan-2-one

A) 27.2 ml ethyl 4-bromobutyrate was added to a suspension of 25 g 4-benzyloxyphenol and 25.7 g ground, dried potassium carbonate in 125 ml DMF. Then the reaction mixture was stirred for 40 h at RT under a protective gas atmosphere. The solid was filtered, and subsequent washing was carried out with MTBE. The filtrate was then reduced under reduced pressure and the remaining residue was taken up with MTBE. The organic phase was washed in succession with water and aqueous common salt solution. The organic phase was then dried over sodium sulfate and evaporated in a vacuum, whereupon the crude product crystallized. Recrystallization from EA/n-hexane with ice cooling yielded 35.8 g ethyl 4-[4-(benzyloxy)phenoxy] butyrate, m.p.=51–52° C.

B) 24.8 g of the product obtained above was dissolved in 115 ml dry glyme, under a protective gas atmosphere, 13.2 ml (trifluoromethyl)trimethylsilane and 126 mg cesium fluoride were added thereto and then the mixture was stirred for 2 h at RT. Then 25 g TBAF was added to this reaction mixture and it was stirred for a further 3 h. Then it was diluted with MTBE and the organic phase was washed with ice water and common salt solution. Then the organic phase was dried over sodium sulfate and evaporated at reduced pressure, whereupon a crystalline residue formed. This residue was recrystallized from EA/n-hexane. 25.6 g of the title compound was obtained, m.p.=51–53° C.

EXAMPLE 4

6,6,6-trifluoro-1-(4-methoxyphenyl)hexane-1,5-dione

A) A solution of 20.7 g 5-(4-methoxyphenyl)-5-oxo-valeric acid (for preparation see Example 2A)) in 200 ml dry dichloromethane was added slowly dropwise under a protective gas atmosphere to 51.8 ml trifluoroacetic anhydride, dissolved in 300 ml dry dichloromethane, with ice cooling, so that the temperature was between 0 and 5° C. Then 45.1 ml pyridine was added dropwise under the same conditions. The reaction mixture was then stirred for one hour at 0° C. and for two hours at RT. The reaction mixture was poured onto ice and the organic phase was washed in succession with water and saturated common salt solution. After drying over sodium sulfate, it was evaporated in a vacuum. Flash chromatography of the resulting residue on silica gel with n-hexane, to which a continuously increased proportion of EA was added, yielded 16.5 g 6-(4-methoxyphenyl)-3,4-dihydro-2H-pyran-2-one, m.p.=77.4–79.8° C.

B) 16.3 g of the product obtained above was dissolved in 100 ml dry glyme, under a nitrogen atmosphere, and then molecular sieve was added thereto. Over a period of 30 minutes a total of 12.3 ml (trifluoromethyl) trimethylsilane was added with stirring. After the addition of a spatula tip of caesium fluoride, the mixture was stirred for 2 h at RT. Then 25.18 g TBAF trihydrate was added and the mixture was stirred for a further 30 minutes. The reaction mixture was taken up with MTBE and the organic phase was washed in succession with water and saturated common salt solution. The organic phase was separated, dried over sodium sulfate and reduced in a vacuum. The resulting residue was flash-chromatographed with a mixture of n-hexane/EA (4:1), to which a constantly increased proportion of EA was added, on silica gel. After evaporating the product fractions, 12.2 g of the title compound was obtained, m.p.=67.5–68.9° C.

The compounds of Formula I listed below in Table 1 can also be prepared according to the processes described above or analogously to these processes.

TABLE 1

Further compounds of Formula I

| Ex. | Pos. A$^1$ | A$^1$ R$^1$ | W | A$^3$ | Y | n | R$^2$ | Z | A$^2$ | M.p.[° C.]; MS m/z; IR [cm$^{-1}$] |
|---|---|---|---|---|---|---|---|---|---|---|
| 5 | 4- | H | B | B | B | 0 | H | O | —(CH$_2$)$_{10}$— | 47–49° C. |
| 6 | 4- | H | B | B | B | 0 | H | B | —(CH$_2$)$_7$— | m/z: 272, 104, 91 |
| 7 | 4- | H | B | B | B | 0 | H | B | —(CH$_2$)$_4$— | m/z: 230, 117, 91 |
| 8 | 4- | H | B | B | B | 0 | H | B | —(CH$_2$)$_9$— | m/z: 300, 133, 117, 91 |
| 9 | 4- | H | B | B | B | 0 | H | B | —(CH$_2$)$_5$— | m/z: 244, 117, 91 |
| 10 | 4- | H | B | B | B | 0 | H | B | —(CH$_2$)$_6$— | m/z: 258, 117, 104, 91 |
| 11 | 4- | —CH$_3$ | B | B | O | 0 | H | B | —(CH$_2$)$_3$— | m/z: 246, 134, 121, 91 |
| 12 | 4- | —C$_6$H$_5$ | B | —CH$_2$— | O | 0 | H | B | —(CH$_2$)$_3$— | 63–65° C. |
| 13 | 4- | H | B | B | B | 0 | H | C(O) | —(CH$_2$)$_4$— | 59–61° C. |
| 14 | 4- | —C$_6$H$_5$ | B | —CH$_2$— | O | 0 | H | B | —(CH$_2$)$_2$— | 66–69° C. |
| 15 | 4- | —CH$_3$ | B | B | B | 0 | H | O | —(CH$_2$)$_3$— | 2927, 1764, 1614, 1513 cm$^{-1}$ |
| 16 | 4- | —C$_6$H$_5$ | B | —(CH$_2$)$_3$— | O | 1 | H | O | —(CH$_2$)$_3$— | m/z: 380, 119, 91 |
| 17 | 4- | 2-naphthyl | B | —(CH$_2$)$_2$— | O | 1 | H | O | —(CH$_2$)$_3$— | 87–82° C. |

TABLE 1-continued

Further compounds of Formula I

A¹

| Ex. | Pos. A¹ | R¹ | W | A³ | Y | n | R² | Z | A² | M.p.[° C.]; MS m/z; IR [cm⁻¹] |
|---|---|---|---|---|---|---|---|---|---|---|
| 18 | 4- | —CH₃ | B | —(CH₂)₇— | O | 1 | H | O | —(CH₂)₃— | m/z: 374, 245, 139, 107 |
| 19 | 4- | —C₆H₅ | B | —(CH₂)₄— | O | 1 | H | O | —(CH₂)₃— | m/z: 394, 245, 139, 131, 107 |
| 20 | 4- | c-C₆H₁₁ | B | —(CH₂)₂— | O | 1 | H | O | —(CH₂)₃— | m/z: 372, 245, 139, 107 |
| 21 | 4- | —C₆H₅ | O | —(CH₂)₇— | O | 1 | H | O | —(CH₂)₃— | 42–44° C. |
| 22 | 4- | —C₆H₅ | B | —CH₂— | O | 0 | H | B | —(CH₂)₄— | 60–63° C. |
| 23 | 4- | —C₆H₅ | O | —(CH₂)₃— | O | 1 | H | O | —(CH₂)₃— | m/z: 396, 261, 139, 123, 107 |
| 24 | 4- | —C₂H₅ | O | —(CH₂)₃— | O | 1 | H | O | —(CH₂)₃— | m/z: 348, 261, 123, 107 |
| 25 | 4- | —CH₃ | B | —(CH₂)₁₀— | O | 1 | H | O | —(CH₂)₃— | 2927, 1765, 1613, 1513 cm⁻¹ |
| 26 | 4- | —CH(CH₃)₂ | B | —(CH₂)₂— | O | 1 | H | O | —(CH₂)₃— | m/z: 332, 245, 139, 107 |
| 27 | 4- | —C₆H₅ | O | —(CH₂)₅— | O | 1 | H | O | —(CH₂)₃— | m/z: 438, 347, 261, 123, 107, 91 |
| 28 | 4- | c-C₆H₁₁ | B | —(CH₂)₄— | O | 1 | H | O | —(CH₂)₃— | m/z: 400, 245, 139, 107 |
| 29 | 4- | —C₆H₅ | B | —CH₂— | O | 0 | H | B | —(CH₂)₅— | 52–54° C. |
| 30 | 4- | —CH₃ | B | B | O | 0 | H | C(O) | —(CH₂)₄— | 84–86° C. |
| 31 | 4- | —CH₃ | B | B | O | 0 | H | B | —(CH₂)₅— | m/z: 274, 121, 91 |
| 32 | 4- | —C₆H₅ | B | —(CH₂)₃— | O | 0 | H | O | —(CH₂)₃— | 32–35° C. |

B = bond,
c = cyclo,
Pos. A¹ = ring position of the group A¹ relative to the group —Z—A²—COCF₃

EXAMPLE 33

6,6,6-trifluoro-1-(3-n-butoxyphenyl)hexane-1,5-dione

A) A mixture of 2.04 g 3-hydroxybenzaldehyde, 9 g dried potassium carbonate, 0.2 g potassium iodide and 2 ml n-butyl bromide were heated to 80° C. under a protective gas atmosphere in 100 ml methyl ethyl ketone for 24 h under reflux cooling. Then once again 1 ml n-butyl bromide was added and the mixture was heated to 80° C. for a further 5 h. After cooling to RT, evaporation was carried out in a water pump vacuum (WV), the residue was taken up with a little n-hexane and 5 g silica gel was added thereto. The mixture thus obtained was again evaporated in the WV. The remaining residue was placed on a chromatographic column and purified by means of flash chromatography (stationary phase: silica gel, mobile phase: pentane/diethyl ether 5:1). 2.5 g 3-n-butoxybenzaldehyde was obtained as oil.

B) 500 mg of the aldehyde obtained above were dissolved in 5 ml dry THF with moisture excluded and under a protective gas atmosphere and 0.05 ml of a 1M TBAF solution in THF was added thereto. Initially 0.5 ml trimethylsilyl cyanide and after one hour another 0.1 ml trimethylsilyl cyanide were added slowly to this initial solution. Then the mixture was cooled to –80° C. and 4 ml of a 1M lithium bis(trimethylsilyl) amide solution in THF was added at this temperature. The resulting reaction mixture was allowed to thaw to RT within 30 minutes and then 0.9 ml ethyl 4-bromobutyrate and a spatula tip of potassium iodide were added. The reaction mixture was heated to boiling under reflux cooling for one hour, 10 ml of a 1M TBAF solution was added thereto and the mixture left to stand for another 1 h at RT. Then the solvent was evaporated in the WV, the remaining residue was taken up in MTBE and the organic phase was washed with water. The organic phase was separated, dried over sodium sulphate and evaporated in the WV. The remaining residue was purified by means of flash chromatography (stationary phase: silica gel; mobile phase: n-pentane/ether 5:1 v/v). 320 mg ethyl 5-(3-n-butoxyphenyl)-5-oxo-valerate was obtained, which was used directly for the subsequent reaction without characterisation.

C) 315.6 mg of the ethyl ester obtained above was dissolved in 10 ml aqueous ethanol and 560 mg solid KOH was added thereto. The resulting reaction mixture was heated to boiling for 2 h under reflux cooling and the volume thereof was then evaporated to about half in the WV. After cooling, 15 ml of an aqueous 1N hydrochloric acid was added to the remaining residue and the aqueous phase was extracted three times with diethyl ether. The combined ether phases were dried over magnesium sulphate and evaporated in the WV. After drying the remaining residue in an oil pump vacuum (OV), 249.8 mg 5-(3-n-butoxyphenyl)-5-oxo-valeric acid was obtained as amorphous solid, which was used directly for the subsequent reaction without characterisation.

D) 240 mg of the acid obtained above were reacted with 5 ml trifluoroacetic anhydride in the manner described above in Example 4A). 121 mg 6-(3-n-butoxyphenyl)-3,4-dihydro-2H-pyran-2-one was obtained.

E) 1.2 g of the pyranone obtained above was reacted with 0.75 ml (trifluoromethyl)trimethylsilane and 1.54 g TBAF trihydrate in the manner described above in Example 4B). 0.8 g of the title compound was obtained as oil, IR (film): 2961, 1764, 1687 cm⁻¹.

EXAMPLE 34

6,6,6-trifluoro-1-(3-benzyloxyphenyl)hexane-1,5-dione

A) 2 ml 3-bromoanisole was added slowly dropwise with moisture excluded and under a protective gas atmosphere to 1.5 g magnesium chippings and 50 ml dry diethyl ether. After the addition of an iodine crystal, a further 7.62 ml bromoanisole was added such that slight boiling was maintained. Then the reaction mixture was heated to boiling for another 2 h under reflux cooling. While boiling was maintained, 5.0 g cyclopentanone was added and allowed to react for 30 minutes at this temperature. Then it was left to stand overnight at RT. The reaction mixture was first cooled with ice and then 50 g ice and 32 ml of a cold aqueous 2.5M sulphuric acid were added. The aqueous phase was separated and extracted twice with 50 ml diethyl ether each time. The combined organic phases were dried over sodium sulphate and evaporated in the WV. The remaining residue was heated for 2 h with 12.5 ml of an aqueous 2.5 M sulphuric acid under reflux cooling. After cooling to RT, it was extracted three times with 20 ml diethyl ether each time and the combined organic phases were dried over sodium sulphate. Evaporation of the excess solvent in the WV and purification of the remaining residue by means of flash chromatography (stationary phase: silica gel, mobile phase: n-heptane) yielded 5.0 g 1-cyclopent-1-en-1-yl-3-methoxybenzene as a light-brownish oil, which was used directly for the reaction given below without characterisation.

B) 5.2 g of the cyclopentene derivative obtained above was stirred with 9.32 g pre-dried pyridinium chloride for 3 hours at 220° C. After cooling to RT, the reaction mixture was poured on to 50 ml 1N aqueous hydrochloric acid. 25 ml saturated common salt solution was added thereto and the aqueous phase was extracted three times with 50 ml MTBE each time. The combined organic phases were dried over sodium sulphate and evaporated in the WV. 4.75 g slightly light brown 3-cyclopent-1-en-1-yl-phenol was obtained, which was used directly for the reaction given below without characterisation.

C) 1.0 g of the cyclopentene derivative obtained above, 0.76 ml benzyl bromide, 1.34 g dried potassium carbonate and 1.24 g potassium iodide were heated to boiling under reflux cooling in 25 ml acetone for 5 h. After cooling to RT, 100 ml water was added and the aqueous phase was extracted three times with MTBE. The combined organic phases were then washed in succession with 0.5 N aqueous sodium hydroxide solution, water and saturated aqueous common salt solution, dried over sodium sulphate and evaporated in the WV. Drying of the remaining residue in the OV yielded 1.48 g 1-(benzyloxy)-3-cyclopent-1-en-1-yl benzene.

D) A mixture of 3.5 g potassium permanganate, 445 mg Aliquat® 336, 30 ml toluene and 35 ml water was added dropwise under a protective gas atmosphere at 0° C. to a solution of 1.0 g of the benzyloxycyclopentenyl derivative obtained above in 5 ml toluene. After 30-minutes' stirring, 1.3 g sodium hydrogen sulphite and 15 ml 6 N aqueous hydrochloric acid were added in succession to this initial solution. It was extracted three times with 50 ml EA each time, the combined organic phases were washed twice with 50 ml 2 N aqueous hydrochloric acid each time and finally once with water and dried over sodium sulphate. The dried organic phase was evaporated in the WV and the remaining residue was purified by means of flash chromatography (stationary phase: silica gel, mobile phase: n-heptane/ethyl acetate 3:1 v/v). After evaporation of the product fractions and drying in the OV, 536 mg 5-(3-benzyloxyphenyl)-5-oxo-valeric acid was obtained as a white solid.

E) 1.9 g of the acid obtained above were reacted with 5.4 ml trifluoroacetic anhydride in the manner described above in Example 4A). 1.79 g 6-(3-benzyloxyphenyl)-3,4-dihydro-2H-pyran-2-one was obtained as brown oil, which was used directly for the reaction given below without further purification or characterisation.

F) 1.0 g of the pyranone obtained above was reacted with 0.53 ml (trifluoromethyl)trimethylsilane, 10 mg caesium fluoride and 1.13 g TBAF trihydrate in the manner described above in Example 4B). 302 mg of the title compound was obtained as a solid, m.p.=75.3–80.3° C.

EXAMPLE 35

6,6,6-trifluoro-1-[4-methoxy-3-(4-phenylbutyl) phenyl]hexane-1,5-dione

A) 4.6 g potassium tert. butylate was dissolved in 165 ml DMF under a protective gas atmosphere. 17.4 g (3-phenylpropyl)triphenylphosphonium bromide was added with ice cooling to this initial solution and it was stirred for 30 minutes. Then a solution of 4.44 ml 2-methoxybenzaldehyde in 30 ml DMF was added dropwise and the reaction mixture was left to stand for 30 minutes with ice cooling and then for another 12 h at RT. Excess DMF was evaporated in the WV, the remaining residue was taken up in MTBE and the organic phase was washed in succession with water and saturated aqueous common salt solution. The organic phase was dried over sodium sulphate and evaporated in the WV. Purification of the remaining residue by means of flash chromatography (stationary phase: silica gel, mobile phase: n-hexane/ethyl acetate 7:3 v/v) yielded 3.5 g 1-methoxy-2-(4-phenylbut-1-enyl)benzene.

B) 3.5 g of the anisole derivative obtained above were dissolved in 100 ml EA, 0.9 g 10% Pd on carbon was added thereto and then hydrogenated for 6 h at a hydrogen pressure of 4.4 bar. After filtering the catalyst, the solvent was evaporated in the WV and the remaining residue was purified by means of flash chromatography (stationary phase: silica gel, mobile phase: n-hexane/EA 8:2 v/v). After evaporating the product fractions and drying in the OV, there was obtained Evaporation of the product fractions and drying in the OV yielded 3.2 g 1-methoxy-2-(4-phenylbutyl)benzene [sic].

F) 3.2 g of the methoxyphenylbutylbenzene derivative obtained above was reacted with 1.6 ml glutaric anhydride and 3.5 g anhydrous aluminium trichloride in the manner described above in Example 2A). 2.7 g. 5-[4-methoxy-3-(4-phenylbutyl)phenyl]-5-oxo-valeric acid was obtained.

C) 2.7 g of the valeric acid derivative obtained above was reacted with 4.2 ml trifluoroacetic anhydride in the manner described above in Example 4A). 1.4 g 5-[4-methoxy-3-(4-phenylbutyl)phenyl] -3,4-dihydro-2H-pyran-2-one was obtained.

D) 1.4 g of the pyranone obtained above was reacted with 0.69 ml (trifluoromethyl)trimethylsilane and 1.3 g TBAF trihydrate in the manner described above in Example 4B). 1.3 g of the title compound was obtained, IR (film): 2934, 1763, 1676 cm$^{-1}$.

EXAMPLE 37

6,6,6-trifluoro-1-[4-(1-naphthyl)phenyl]hexane-1,5-dione 1.0 g 1-naphthaleneboronic acid, 1.0 g potassium carbonate and 0.06 g tetrakis(triphenylphosphine)palladium(0) in 90 ml toluene were combined under a protective gas atmosphere. A solution of 1.0 g 1-(4-bromophenyl)-6,6,6-trifluorohexane-1,5-dione in 10 ml toluene was added dropwise to this initial solution and it was stirred for 3 days at 90° C. It was allowed to cool to RT, 13 ml saturated aqueous sodium hydrogen carbonate solution was added dropwise thereto and the phases were separated. The organic phase was washed in succession with water, aqueous potassium hydrogen sulphate solution, water and saturated aqueous common salt solution. The organic phase was dried over sodium sulphate and the solvent was evaporated in the WV. Purification of the remaining residue by means of flash chromatography (stationary phase: silica gel, mobile phase: n-hexane/EA 3:2 v/v) and subsequent recrystallisation of the combined product fractions from EA/n-hexane (2:3) yielded 0.75 g of the title compound, m.p.=79.7–82.5° C.

EXAMPLE 38

6,6,6-trifluoro-1-(4-methoxyphenyl)-2-(4-phenoxybutyl)hexane-1,5-dione

A) 25 ml glutaric acid monoethylester chloride was dissolved in 250 ml dry dichloromethane. First of all 26 ml anisole was added dropwise with ice cooling, then 42.4 g aluminium trichloride was added in portions such that the reaction temperature did not exceed 10° C. The red-coloured solution was stirred for 3 h at 0° C. and then poured on to dilute aqueous hydrochloric acid to which ice had been added. The organic phase was separated, washed in succession with water and with saturated aqueous common salt solution and dried over sodium sulphate. The organic phase was evaporated in the WV and the remaining residue was recrystallised from MTBE. 38.8 g ethyl 5-(4-methoxyphenyl)-5-oxo-valerate, m.p.= 56.6–58.1° C., was obtained.

B) 4.0 g of the valerate obtained above was dissolved in 100 ml dry DMF under a protective gas atmosphere. 0.7 g sodium hydride (60%-strength) was added thereto with ice cooling and the mixture was stirred for another 30 minutes at 0° C. A solution of 4.2 g 4-phenoxy-1-bromobutane in 40 ml dry DMF was added dropwise to this initial solution at 0–5° C. Then the reaction mixture was stirred for 1 hour at 0° C., 1 hour at room temperature and finally 2 h at 50° C. After cooling to RT, it was left to stand for another 16 h before the reaction mixture was poured on to saturated aqueous potassium hydrogen sulphate solution mixed with ice and the aqueous phase was extracted twice with 70 ml EA each time. The combined organic phases were then washed in succession with water and with saturated aqueous common salt solution, dried over sodium sulphate and evaporated in the WV. The remaining residue was purified by means of flash chromatography (stationary phase: silica gel; mobile phase: n-hexane, which was gradually replaced by EA). The combined product fractions were evaporated in the WV and were distilled on a bulb tube at 250° C. and 2 mbar. 3.0 g ethyl-4-(4-methoxyphenyl)-8-phenoxyoctanoate was obtained.

C) 3.0 mg of the ethylmethoxyphenyl phenoxyoctanoate obtained above was dissolved in 20 ml methanol and a solution of 8.5 mg solid KOH in 30 ml water was added thereto. The reaction mixture was stirred for 16 h at RT and was then extracted with 100 ml MTBE. The aqueous phase was acidulated with dilute aqueous hydrochloric acid and extracted three times with 70 ml MTBE each time. Then the organic phase was washed in succession with water and with saturated aqueous common salt solution, dried over sodium sulphate and evaporated in the WV. The remaining residue was purified by means of flash chromatography (stationary phase: silica gel, mobile phase: first n-hexane/EE 4:1, which was gradually replaced by pure EA). Drying of the product fractions yielded 1.8 g 4-(4-methoxybenzoyl)-8-phenoxyoctanoic acid.

D) 1.6 g of the methoxybenzoyl phenoxyoctanoic acid derivative obtained above were reacted with 0.66 ml trifluoroacetic anhydride in the manner described above in Example 4A). 1.2 g 6-(4-methoxyphenyl)-5-(4-phenoxybutyl)-3,4-dihydro-2H-pyran-2-one was obtained as oil, IR 2937, 1764, 1586 $cm^{-1}$.

E) 1.5 g of the pyranone obtained above were reacted with 0.66 ml (trifluoromethyl)trimethylsilane and 1.34 g TBAF trihydrate in the manner described above in Example 4B). 1.5 g of the title compound was obtained, IR (film): 2941, 1763, 1670 $cm^{-1}$.

The compounds of Formula I listed below in Table 2 can also be prepared according to the processes described above or analogously to these processes.

TABLE 2

Further compounds of Formula I:

| Ex. | Pos. $A^1$ | $R^1$ | W | $A^3$ | Y | n | $R^2$ | Z | $A^2$ | M.p.[° C.]: MS m/z: IR[$cm^{-1}$] |
|---|---|---|---|---|---|---|---|---|---|---|
| 39 | 4- | —$C_6H_5$ | B | —$(CH_2)_3$— | O | 0 | H | O | —$(CH_2)_5$— | 46–50° C. |
| 40 | 4- | —$CH_3$ | B | —$(CH_2)_7$— | O | 0 | H | O | —$(CH_2)_3$— | 37–40° C. |
| 41 | 4- | c-$C_6H_{11}$ | B | —$CH_2$— | O | 0 | H | O | —$(CH_2)_3$— | 2926, 1764, 1509 $cm^{-1}$ |
| 42 | 4- | —$C_6H_5$ | O | —$(CH_2)_4$— | O | 0 | H | O | —$(CH_2)_3$— | 104–107° C. |
| 43 | 4- | —$C_6H_5$ | B | —$CH_2$— | O | 0 | H | C(O) | —$(CH_2)_3$— | 72.3–73.1° C. |
| 44 | 4- | —$CH_3$ | B | B | O | 0 | H | C(O) | (n-$C_5H_{11}$—)CH—$(CH_2)_2$— | 2933, 1764, 1671 $cm^{-1}$ |
| 45 | 4- | —$C_6H_5$ | B | —$(CH_2)_3$— | O | 0 | H | B | —$(CH_2)_4$— | 2938, 1764, 1512 $cm^{-1}$ |
| 46 | 3- | —$CH_3$ | B | —$(CH_2)_{10}$— | O | 0 | H | B | —$(CH_2)_4$— | 2855, 1765, 1608 $cm^{-1}$ |
| 47 | 4- | —$CH_3$ | B | B | O | 0 | H | C(O) | ($C_6H_5$-n-$C_3H_6$—)CH—$(CH_2)_2$— | 2936, 1763, 1670 $cm^{-1}$ |
| 48 | 4- | —$CH(CH_3)_2$ | B | —$(CH_2)_3$— | B | 0 | H | B | —$(CH_2)_4$— | 2930, 1765, 1514 $cm^{-1}$ |
| 49 | 4- | —$C_6H_5$ | O | —$(CH_2)_4$— | O | 0 | H | B | —$(CH_2)_4$— | 21–30° C. |
| 50 | 3- | —$CH(CH_3)_2$ | B | —$(CH_2)_3$— | B | 0 | H | B | —$(CH_2)_4$— | 2932, 1765, 1607 $cm^{-1}$ |
| 51 | 4- | —$CH_3$ | B | B | O | 0 | H | C(O) | (n-$C_{10}H_{21}$—)CH—$(CH_2)_2$— | 2927, 1764, 1670 $cm^{-1}$ |
| 52 | 4- | —$CH_3$ | B | —$(CH_2)_{10}$— | B | 0 | H | B | —$(CH_2)_4$— | 2926, 1765, 1514 $cm^{-1}$ |
| 53 | 4- | —$C_6H_5$ | B | —$(CH_2)_4$— | B | 0 | H | B | —$(CH_2)_4$— | 2932, 1763, 1604 $cm^{-1}$ |
| 54 | 4- | —$C_6H_5$ | O | —$(CH_2)_4$— | O | 0 | H | C(O) | —$(CH_2)_3$— | 78.8–80.4° C. |
| 55 | 4- | —$C_6H_5$ | B | —$(CH_2)_3$— | O | 0 | H | C(O) | —$(CH_2)_3$— | 52.6–54.5° C. |
| 56 | 4- | —$C_6H_5$ | B | B | B | 0 | H | B | —$(CH_2)_4$— | 2935, 1763, 1709 $cm^{-1}$ |
| 57 | | H | B | B | B | 0 | | C(O) | —$(CH_2)_3$— | 1764, 1687, 1586 $cm^{-1}$ |
| 58 | 3- | —$C_6H_5$ | B | —$(CH_2)_2$— | B | 0 | 6-$OCH_3$ | C(O) | —$(CH_2)_3$— | 2944, 1763, 1671 $cm^{-1}$ |
| 59 | 3- | —$CH(CH_3)_2$ | B | —$(CH_2)_3$— | B | 0 | 6-$OCH_3$ | C(O) | —$(CH_2)_3$— | 35.3–36.5° C. |
| 60 | 4- | | (4)-$(CH_2)_4$—(3) | | | | | C(O) | —$(CH_2)_3$— | 2936, 1763. 1681, 1605, 1572 $cm^{-1}$ |
| 61 | 4- | | (4)-O—$(CH_2)_2$—(3) | | | | | C(O) | —$(CH_2)_3$— | 68.8–69.5° C. |
| 62 | 4- | 2-naphthyl | B | B | B | 0 | H | C(O) | —$(CH_2)_3$— | 1761, 1673, 1606 $cm^{-1}$ |
| 63 | 4- | —$CH_3$ | B | —$(CH_2)_{15}$— | O | 0 | H | C(O) | —$(CH_2)_3$— | 67.7–68.9° C. |
| 64 | 3- | —$CH_3$ | B | —$(CH_2)_{10}$— | B | 0 | 4-$OCH_3$ | C(O) | —$(CH_2)_3$— | 2925, 1764, 1674 $cm^{-1}$ |
| 65 | 4- | —$CH_3$ | B | —$(CH_2)_{13}$— | O | 0 | H | C(O) | —$(CH_2)_3$— | 63.3–65.0° C. |

B = bond,
c = cyclo,
Pos. $A^1$ = ring position of the group $A^1$ relative the group —Z—$A^2$—$COCF_3$

EXAMPLE I

Capsules containing 6,6,6-trifluoro-1-(4-methoxyphenyl)hexane-1,5-dione

Capsules with the following composition per capsule were produced:

| | |
|---|---|
| 6,6,6-trifluoro-1-(4-methoxyphenyl)hexane-1,5-dione | 20 mg |
| Corn starch | 60 mg |
| Lactose | 300 mg |
| Ethyl acetate | q.s. |

The active substance, the corn starch and the lactose were processed into a homogenous pasty mixture using ethyl acetate. The paste was ground and the resulting granules were placed on a suitable tray and dried at 45° C. in order to remove the solvent. The dried granules were passed through a crusher and mixed in a mixer with the further following auxiliaries:

| | |
|---|---|
| Talcum | 5 mg |
| Magnesium stearate | 5 mg |
| Corn starch | 9 mg | and then poured into 400 mg capsules (=capsule size 0).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method of treating or inhibiting obesity, metabolic syndrome hypotension, insulin resistance, dyslipoproteinaemia or hyperuricaemia in a mammal, said method comprising administering to said mammal an effective amount of a compound corresponding to formula I,

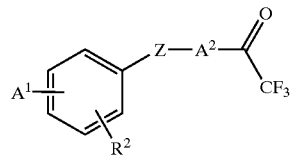

I wherein
A$^1$ is a group of the formula R$^1$—W—A$^3$—Y—(CH$_2$)$_n$—, wherein
R$^1$ is hydrogen,
lower alkyl,
C$_{3-7}$-cycloalkyl,
phenyl-C$_{0-4}$-alkyl or
naphthyl;
W is a bond or oxygen;
A$^3$ is a bond or C$_{1-20}$-alkylene;
Y is a bond or oxygen and
n is a whole number from 0 to 3;
R$^2$ is hydrogen, lower alkyl, lower alkoxy or halogen, or
A$^1$ and R$^2$, together with the carbon atoms to which they are bonded, form a C$_{5-7}$-cycloalkyl group;
Z is a bond, oxygen or carbonyl and A$^2$ is C$_{1-20}$-alkylene.

2. The method of claim 1, wherein R$^1$ is phenyl-C$_{0-4}$-alkyl which is substituted in the phenyl ring by lower alkylenedioxy or one to two times by lower alkyl, lower alkoxy, halogen or perfluoro-lower alkyl.

3. The method of claim 1, wherein A$^3$ is C$_{1-20}$-alkylene which is substituted one to two times by phenyl, naphthyl, lower alkyl or C$_{5-7}$-cycloalkyl.

4. The method of claim 1, wherein A$^1$ and R$^2$, together with the carbon atoms to which they are bonded, form a C$_{5-7}$-cycloalkyl group, the sp$^3$-hybridized carbon atoms of which are replaced one to two times by oxygen.

5. The method of claim 1, wherein A$^2$ is C$_{1-20}$-alkylene which is substituted once by C$_{1-12}$-alkyl, C$_{1-12}$-alkyl-phenyl or C$_{1-12}$-alkyloxyphenyl.

6. The method of claim 1, wherein said compound is present in the form of a solvate.

7. The method of claim 1, wherein said compound is present in the form of a hydrate.

8. The method of claim 1, wherein R$^2$ is hydrogen or halogen.

9. The method of claim 1, wherein the group A$^1$ is located in the para position relative to the radical —Z—A$^2$—C(O)—CF$_3$.

10. A method for inhibiting pancreatic lipase, the method comprising administering to a subject in need thereof a pancreatic lipase inhibiting amount of a compound corresponding to formula If

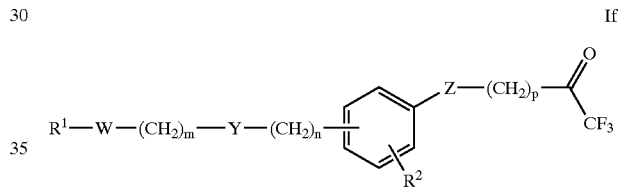

If wherein
R$^1$ is hydrogen,
lower alkyl,
C$_{3-7}$-cycloalkyl,
phenyl-C$_{0-4}$-alkyl or
naphthyl;
R$^2$ is hydrogen, lower alkyl, lower alkoxy or halogen;
W is a bond or oxygen;
Y is a bond or oxygen;
Z is a bond, oxygen or carbonyl;
m is a whole number from 0 to 10;
n is a whole number from 0 to 3 and
p is a whole number from 1 to 20.

11. The method of claim 10, wherein R$^1$ is phenyl-C$_{0-4}$-alkyl which is substituted in the phenyl ring by lower alkylenedioxy or one to two times by lower alkyl, lower alkoxy, halogen or perfluoro-lower alkyl.

12. A compound selected from the group consisting of:
5-[4-(benzyloxymethyl)-phenoxy]-1,1,1-trifluoropentan-2-one,
5-[4-(benzyloxy)phenoxy]-1,1,1-trifluoropentan-2-one,
1,1,1-trifluoro-12-phenoxy-dodecan-2-one and
1,1,1-trifluoro-5-[4-(3-phenylpropoxy)phenoxy]pentan-2-one.

13. A compound which is
6-(4-methoxyphenyl)-1,1,1-trifluorohexan-2-one.

14. A compound selected from the group consisting of:
1,1,1-trifluoro-9-phenyl-nonan-2-one;
1,1,1-trifluoro-11-phenyl-undecan-2-one and
1,1,1-trifluoro-8-phenyl-octan-2-one.

15. A method of treating or inhibiting obesity, metabolic syndrome hypotension, insulin resistance, dyslipoproteinaemia or hyperuricaemia in a mammal, said method comprising administering to said mammal an effective amount of a compound corresponding to formula Ig,

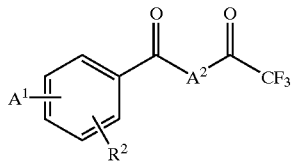

Ig wherein $A^1$ is a group corresponding to formula $R^1$—W—$A^3$—Y—$(CH_2)_n$—, wherein
  $R^1$ is hydrogen,
    lower alkyl,
    $C_{3-7}$-cycloalkyl,
    phenyl-$C_{0-4}$-alkyl or
    naphthyl;
  W is a bond or oxygen;
  $A^3$ is a bond or $C_{1-20}$-alkylene;
  Y is a bond or oxygen and
  n is a whole number from 0 to 3;
$R^2$ is hydrogen, lower alkyl, lower alkoxy or halogen or
$A^1$ and $R^2$, together with the carbon atoms to which they are bonded form a
  $C_{5-7}$-cycloalkyl group and
$A^2$ is $C_{1-20}$-alkyl.

16. A compound corresponding to formula Ig,

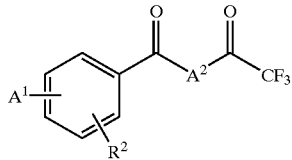

Ig wherein $A^1$ is a group corresponding to formula $R^1$—W—$A^3$—Y—$(CH_2)_n$—, wherein
  $R^1$ is phenyl-$C_{0-4}$-alkyl which is substituted in the phenyl ring by lower alkylenedioxy or one to two times by lower alkyl, lower alkoxy, halogen or perfluoro-lower alkyl
  W is a bond or oxygen;
  $A^3$ is a bond or $C_{1-2}$-alkylene;
  Y is a bond or oxygen and
n is a whole number from 0 to 3;
$R^2$ is hydrogen, lower alkyl, lower alkoxy or halogen or
$A^1$ and $R^2$, together with the carbon atoms to which they are bonded form a
$C_{5-7}$-cycloalkyl group and
$A^2$ is $C_{1-20}$-alkyl.

17. A compound corresponding to formula Ig,

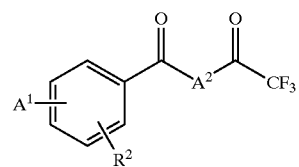

Ig wherein $A^1$ is a group corresponding to formula $R^1$—W—$A^3$—Y—$(CH_2)_n$—, wherein
  $R^1$ is hydrogen,
    lower alkyl,
    $C_{3-7}$-cycloalkyl,
    phenyl-$C_{0-4}$-alkyl or
    naphthyl;
  W is a bond or oxygen;
  $A^3$ is a bond or $C_{1-20}$-alkylene which is substituted one to two times by phenyl, naphthyl, lower alkyl or $C_{5-7}$-cycloalkyl;
  Y is a bond or oxygen and
  n is a whole number from 0 to 3;
$R^2$ is hydrogen, lower alkyl, lower alkoxy or halogen or
$A^1$ and $R^2$, together with the carbon atoms to which they are bonded form a
$G_{5-7}$-cycloalkyl group and
$A^2$ is $C_{1-20}$-alkyl.

18. A compound corresponding to formula Ig,

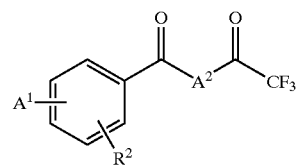

Ig wherein $A^1$ is a group corresponding to formula $R^1$—W—$A^3$—Y—$(CH_2)_n$—, wherein
  $R^1$ is hydrogen,
    lower alkyl,
    $C_{3-7}$-cycloalkyl,
    phenyl-$C_{0-4}$-alkyl or
    naphthyl;
  W is a bond or oxygen;
  $A^3$ is a bond or $C_{1-20}$-alkylene;
  Y is a bond or oxygen and
  n is a whole number from 0 to 3;
$R^2$ is hydrogen, lower alkyl, lower alkoxy or halogen and
$A^1$ and $R^2$, together with the carbon atoms to which they are bonded, form a $C_{5-7}$-cycloalkyl group, the sp$^3$-hybridized carbon atoms of which are replaced one to two times by oxygen and
$A^2$ is $C_{1-20}$-alkyl.

19. A compound corresponding to formula Ig,

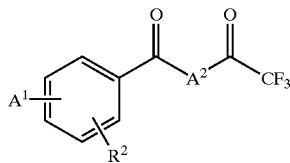

wherein $A^1$ is a group corresponding to formula $R^1$—W—$A^3$—Y—$(CH_2)_n$—, wherein
  $R^1$ is hydrogen,
    lower alkyl,
    $C_{3-7}$-cycloalkyl,
    phenyl-$C_{0-4}$-alkyl or
    naphthyl;
  W is a bond or oxygen;
  $A^3$ is a bond or $C_{1-20}$-alkylene;
  Y is a bond or oxygen and
  n is a whole number from 0 to 3;
$R^2$ is hydrogen, lower alkyl, lower alkoxy or halogen or
$A^1$ and $R^2$, together with the carbon atoms to which they are bonded form a
$C_{5-7}$-cycloalkyl group and
$A^2$ is $C_{1-20}$-alkyl which is substituted once by $C_{1-12}$-alkyl, $C_{1-12}$alkyl-phenyl or $C_{1-12}$-alkyl-oxyphenyl.

20. A compound corresponding to formula Ig,

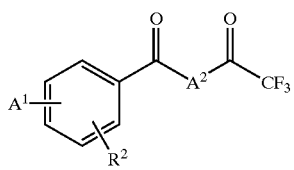

wherein $A^1$ is a group corresponding to formula $R^1$—W—$A^3$—Y—$(CH_2)_n$—, wherein
  $R^1$ is hydrogen,
    lower alkyl,
    $C_{3-7}$-cycloalkyl,
    phenyl-$C_{0-4}$-alkyl or
    naphthyl;
  W is a bond or oxygen;
  $A^3$ is a bond or $C_{1-20}$-alkylene;
  Y is a bond or oxygen and
  n is a whole number from 0 to 3;
$R^2$ is hydrogen, lower alkyl, lower alkoxy or halogen or
$A^1$ and $R^2$, together with the carbon atoms to which they are bonded form a
$C_{5-7}$-cycloalkyl group and
$A^2$ is $C_{1-20}$-alkyl
wherein said compound is present in the form of a solvate or a hydrate.

21. A compound corresponding to formula Ig,

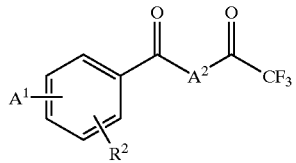

wherein $A^1$ is a group corresponding to formula $R^1$—W—$A^3$—Y—$(CH_2)_n$—, wherein
  $R^1$ is hydrogen,
    lower alkyl,
    $C_{3-7}$-cycloalkyl,
    phenyl-$C_{0-4}$-alkyl or
    naphthyl;
  W is a bond or oxygen;
  $A^3$ is a bond or $C_{1-20}$-alkylene;
  Y is a bond or oxygen and
  n is a whole number from 0 to 3;
$R^2$ is hydrogen, lower alkyl, lower alkoxy or halogen or
$A^1$ and $R^2$, together with the carbon atoms to which they are bonded form a
$C_{5-7}$-cycloalkyl group and
$A^2$ is substituted n-propylene.

22. A compound according to claim 21, wherein said compound is selected from the group consisting of:
  6,6,6-trifluoro-1-(4-methoxyphenyl)hexane-1,5-dione;
  6,6,6-trifluoro-1-(4-(4-phenoxybutoxy)phenyl)hexane-1,5-dione;
  6,6,6-trifluoro-1-(4-(3-phenylpropoxy)phenyl)hexane-1,5-dione;
  1-(4-bromophenyl)-6,6,6-trifluorohexane-1,5-dione;
  6,6,6-trifluoro-1-(4-(1-naphthyl)phenyl)hexane-1,5-dione;
  6,6,6-trifluoro-1-(5,6,7,8-tetrahydronaphthalen-2-yl)hexane-1,5-dione;
  6,6,6-trifluoro-1-(4-(4-methoxy-1-naphthyl)phenyl)hexane-1,5-dione;
  6,6,6-trifluoro-1-(4-(2-naphthyl)phenyl)hexane-1,5-dione;
  6,6,6-trifluoro-1-(4-(hexadecyloxy)phenyl)hexane-1,5-dione and
  6,6,6-trifluoro-1-(4-(tetradecyloxy)phenyl)hexane-1,5-dione.

23. A method of treating or inhibiting obesity, metabolic syndrome hypotension, insulin resistance, dyslipoproteinaemia or hyperuricaemia in a mammal, said method comprising administering to said mammal an effective amount of a compound corresponding to formula Id,

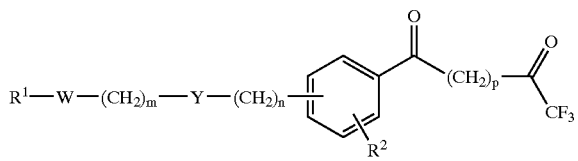

wherein
  $R^1$ is hydrogen, lower alkyl,
$C_{3-7}$-cycloalkyl,
phenyl-$C_{0-4}$-alkyl or
naphthyl;
$R^2$ is hydrogen, lower alkyl, lower alkoxy or halogen;
W is a bond or oxygen;
Y is a bond or oxygen;
m is a whole number from 0 to 10;
n is a whole number from 0 to 3 and
p is a whole number from 1 to 20.

24. A compound corresponding to formula Id,

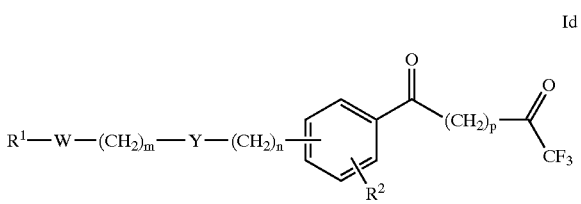

Id wherein
$R^1$ is phenyl-$C_{0-4}$-alkyl which is substituted in the phenyl ring by lower alkylenedioxy or one to two times by lower alkyl, lower alkoxy, halogen or perfluoro-lower alkyl;
$R^2$ is hydrogen, lower alkyl, lower alkoxy or halogen;
W is a bond or oxygen;
Y is a bond or oxygen;
m is a whole number from 0 to 10;
n is a whole number from 0 to 3 and
is a whole number from 1 to 20.

25. A compound selected from the group consisting of 1,1,1-trifluoro-7-phenyl-heptan-2-one and 1,1,1-trifluoro-8-phenyl-octan-2-one.

26. A process for the preparation of compounds of corresponding to formula I',

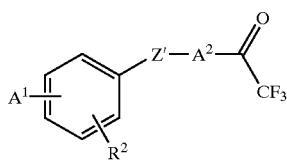

I' wherein
$A^1$ is a group corresponding to formula $R^1$—W—$A^3$—Y—$(CH_2)_n$—, wherein
$R^1$ is hydrogen,
lower alkyl,
$C_{3-7}$-cycloalkyl,
phenyl-$C_{0-4}$-alkyl or
naphthyl;
W is a bond or oxygen;
$A^3$ is a bond or $C_{1-20}$-alkylene;
Y is a bond or oxygen and
n is a whole number from 0 to 3;
$R^2$ is hydrogen, lower alkyl, lower alkoxy or halogen, or
$A^1$ and $R^2$, together with the carbon atoms to which they are bonded, form a $C_{5-7}$-cycloalkyl group;

Z' is carbonyl and
$A^2$ is $C_{1-20}$-alkylene,
comprising the steps of:
reacting a compound of corresponding to formula XIb'

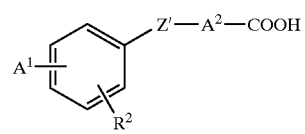

XIb' with an acetic anhydride compound and
reacting cyclic En-lactones obtained as intermediate products with (trifluoromethyl)trimethylsilane.

27. The process of claim 26, wherein $R^1$ is phenyl-$C_{0-4}$-alkyl which is substituted in the phenyl ring by lower alkylenedioxy or one to two times by lower alkyl, lower alkoxy, halogen or perfluoro-lower alkyl.

28. The process of claim 26, wherein $A^3$ is a bond or $C_{1-20}$-alkylene which is substituted one to two times by phenyl, naphthyl, $C_{1-4}$-alkyl or $C_{5-7}$-cycloalkyl.

29. The process of claim 26, wherein $A^1$ and $R^2$, together with the carbon atoms to which they are bonded, form a $C_{5-7}$-cycloalkyl group, the sp$^3$-hybridized carbon atoms of which are replaced one to two times by oxygen.

30. The process of claim 26, wherein $A^2$ is $C_{1-20}$-alkylene which is substituted once by $C_{1-12}$-alkyl, $C_{1-12}$-alkyl-phenyl or $C_{1-12}$-alkyl-oxyphenyl.

31. A pharmaceutical composition comprising as an active ingredient a pharmaceutically effective amount of a compound corresponding to formula Ig,

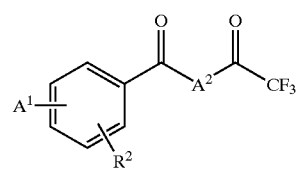

Ig wherein
$A^1$ is a group corresponding to formula $R^1$—W—$A^3$—Y—$(CH_2)_n$—, wherein
$R^1$ is hydrogen,
lower alkyl,
$C_{3-7}$-cycloalkyl,
phenyl-$C_{0-4}$-alkyl or
naphthyl;
W is a bond or oxygen;
$A^3$ is a bond or $C_{1-20}$-alkylene;
Y is a bond or oxygen and
n is a whole number from 0 to 3;
$R^2$ is hydrogen, lower alkyl, lower alkoxy or halogen or
$A^1$ and $R^2$, together with the carbon atoms to which they are bonded form a
$C_{5-7}$-cycloalkyl group;
$A^2$ is $C_{1-20}$-alkyl and
a pharmaceutically acceptable carrier or adjuvant.

* * * * *